(12) United States Patent
Perez-Cruet et al.

(10) Patent No.: US 8,425,546 B2
(45) Date of Patent: Apr. 23, 2013

(54) UP CUTTING KNIFE WITH SUCTION

(75) Inventors: Miguelangelo J. Perez-Cruet, Bloomfield, MI (US); John R. Pepper, Cheshire, CT (US); John A. Miller, Bloomfield Village, MI (US)

(73) Assignee: MI4Spine, LLC, Bloomfield Hills, MI (US)

( * ) Notice: Subject to any disclaimer, the term of this patent is extended or adjusted under 35 U.S.C. 154(b) by 30 days.

(21) Appl. No.: 13/015,257

(22) Filed: Jan. 27, 2011

(65) Prior Publication Data
US 2012/0197279 A1 Aug. 2, 2012

(51) Int. Cl.
*A61B 17/32* (2006.01)
(52) U.S. Cl.
USPC .......................................................... 606/170
(58) Field of Classification Search .......... 606/167–180, 606/184, 185, 79–83; 604/22; 30/349
See application file for complete search history.

(56) References Cited

U.S. PATENT DOCUMENTS

| 5,593,416 | A | * | 1/1997 | Donahue | 606/170 |
| 6,676,677 | B2 | * | 1/2004 | Klein | 606/171 |
| 6,783,533 | B2 | * | 8/2004 | Green et al. | 606/80 |
| 2005/0070818 | A1 | * | 3/2005 | Mueller | 600/564 |
| 2005/0159767 | A1 | * | 7/2005 | Adams et al. | 606/180 |
| 2012/0191117 | A1 | * | 7/2012 | Palmer et al. | 606/170 |

* cited by examiner

*Primary Examiner* — Ryan Severson
*Assistant Examiner* — Anh Dang
(74) *Attorney, Agent, or Firm* — John A. Miller; Miller IP Group, PLC

(57) ABSTRACT

An up-cutting knife that has particular application for minimally invasive spinal surgical procedures. The knife includes an elongated tube that is operable to be inserted through a tubular retractor used in minimally invasive surgical procedures. One end of the elongated tube includes a curved head portion having a cutting blade formed on a top surface thereof and a suction port, and an opposite end of the tube is coupled to a handle having a chamber. A suction device can be coupled to an outlet port in the handle that causes blood and other surgical material to be drawn through the tube and out of the handle.

18 Claims, 2 Drawing Sheets

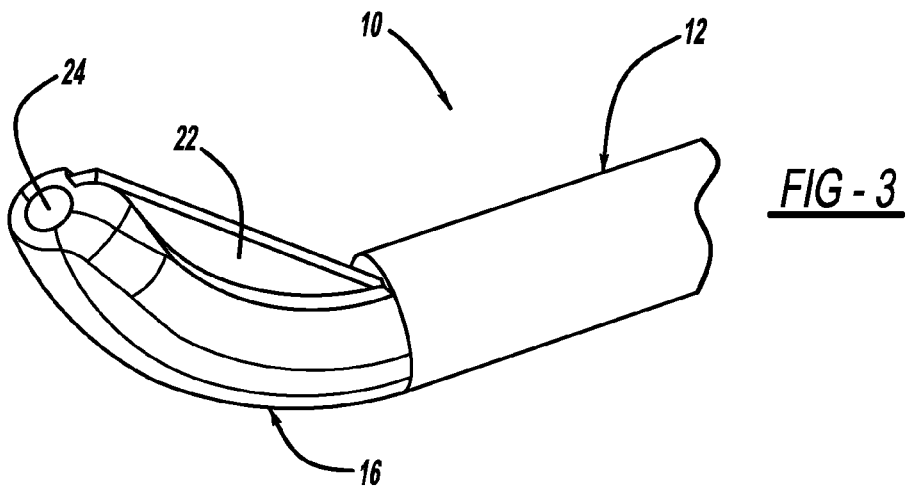
*FIG - 3*
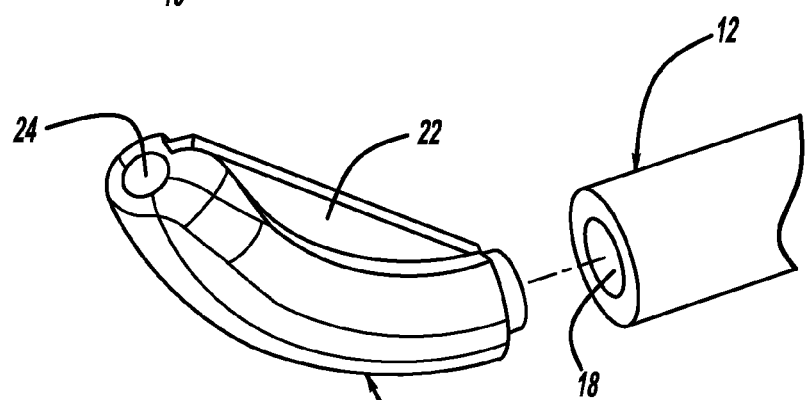
*FIG - 4*
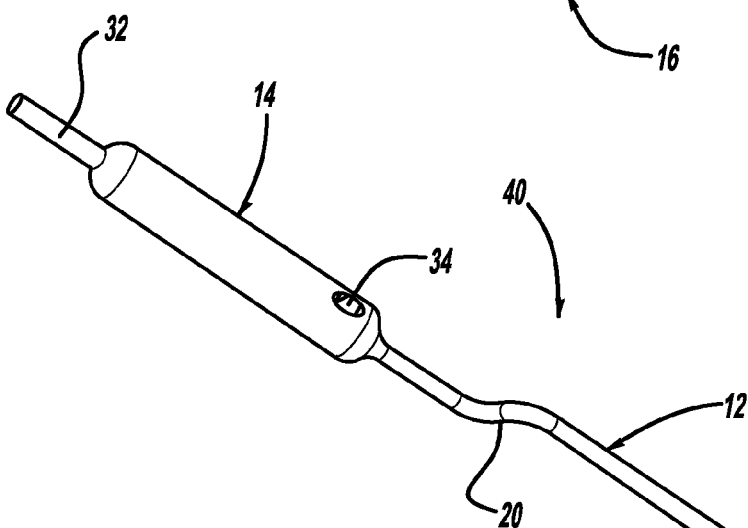
*FIG - 5*
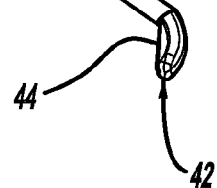

UP CUTTING KNIFE WITH SUCTION

BACKGROUND OF THE INVENTION

1. Field of the Invention

This invention relates generally to a surgical knife that also provides suction and, more particularly, to a surgical knife that includes a curved knife head with a cutting blade formed on a top surface of the head and a suction channel extending therethrough, where the knife has specific application for minimally invasive spinal surgical procedures.

2. Discussion of the Related Art

In an attempt to preserve normal anatomical structures during spine surgery, minimally invasive surgical procedures have been devised. These procedures include lumbar laminectomy for stenosis, cervical laminectomy, lumbar disectomy, spinal fusion, etc. Such procedures typically involve the use of a series of muscle dilators that separate the muscle fibers of the spine to create a pathway to the spine. A Kirschner (K-wire) is initially introduced through a small incision and directed towards the spinal pathology. The position of the K-wire is visualized by a fluoroscopic imaging system to identify its location. An initial narrow diameter muscle dilator is passed over the K-wire, and the K-wire is removed and subsequent larger muscle dilators are continually passed. When the opening is large enough, an access tube or retractor is positioned around the last muscle dilator through which the surgery is performed. The inner sequential muscle dilators are then removed allowing the surgeon to operate through the tubular retractor. The retractors come in a variety of lengths and diameters for different patients and procedures.

There are many surgical instruments that are specially designed for minimally invasive spinal surgical procedures that allow the surgeon to operate through the tubular retractor. These various instruments include retractors, suction devices, drills, cutting tools, etc. that allows the surgeon to perform the surgical procedure in the minimal space provided. Often, more than one of these instruments needs to be inserted through the tubular retractor at the same time to perform a particular procedure. Further, the various instruments that are used during the surgical procedure may be harmful to certain anatomies, such as the dural sac, nerves, etc.

SUMMARY OF THE INVENTION

In accordance with the teachings of the present invention, an up-cutting knife is disclosed that has particular application for minimally invasive spinal surgical procedures. The knife includes an elongated tube that is operable to be inserted through a tubular retractor used in minimally invasive surgical procedures. One end of the elongated tube includes a curved head portion having a cutting blade formed on a top surface thereof and a suction port, and an opposite end of the tube is coupled to a handle having a chamber. A suction device can be coupled to an outlet port in the handle that causes blood and other surgical material to be drawn through the tube and out of the handle.

Additional features of the present invention will become apparent from the following description and appended claims, taken in conjunction with the accompanying drawings.

BRIEF DESCRIPTION OF THE DRAWINGS

FIG. 3 is a cut-away perspective view of a cutting end of the knife shown in FIG. 1;

FIG. 4 is a cut-away, blown-apart, perspective view of the cutting end of the knife shown in FIG. 1; and FIG. 5 is a perspective view of an up-cutting knife having an oppositely oriented cutting end than the knife shown in FIG. 1.

DETAILED DESCRIPTION OF THE EMBODIMENTS

The following discussion of the embodiments of the invention directed to an up-cutting knife with suction for minimally invasive surgical procedures is merely exemplary in nature, and is no way intended to limit the invention or its application or uses. For example, the knife discussed below has particular application for minimally invasive surgical procedures performed through a tubular retractor. However, as will be appreciated by those skilled in the art, the knife disclosed herein may have application for other surgical procedures.

Figure 1:
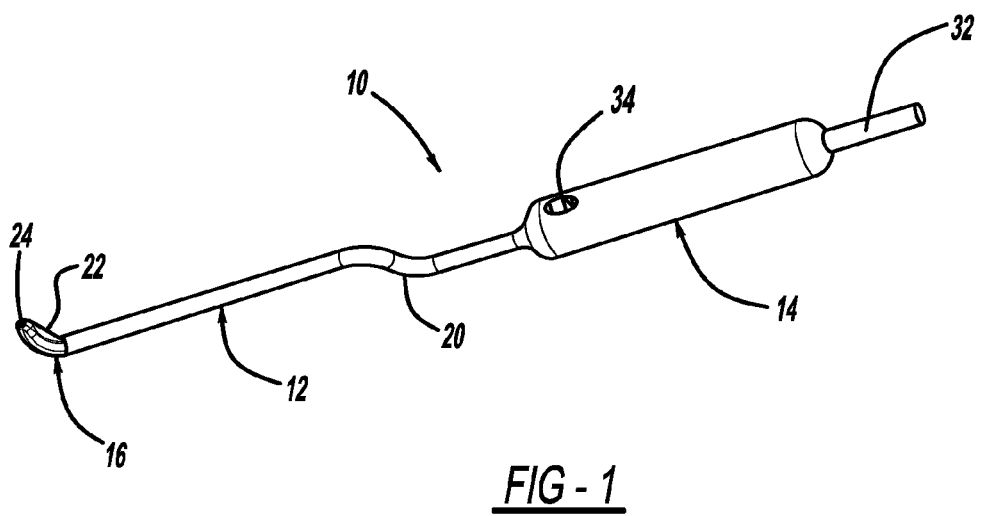
FIG. 1 is a perspective view of an up-cutting knife with suction.
Figure 2:
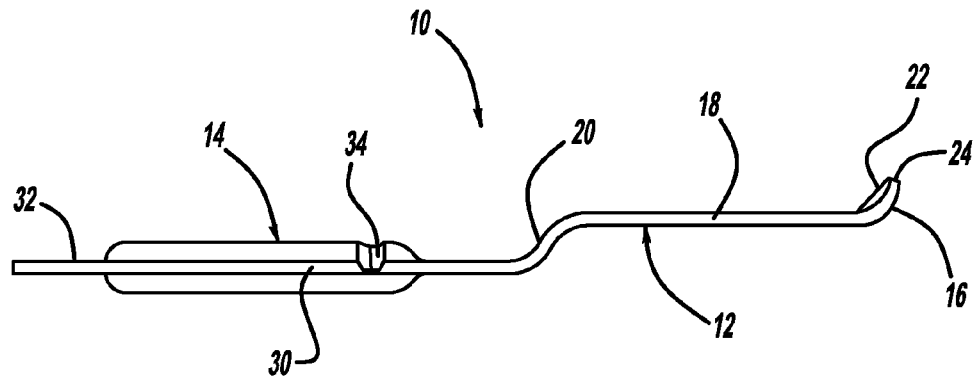
FIG. 2 is a cross-sectional view of the up cutting knife shown in FIG. 1.

FIG. 1 is a perspective view and FIG. 2 is a cross-sectional view of an up-cutting knife 10 that has particular application for minimally invasive spinal surgical procedures being performed through a tubular retractor of the type discussed above. The knife 10 includes an elongated tube 12 having an internal bore 18. A cylindrical handle 14 is coupled to one end of the tube 12 and a cutting head 16 is coupled to an opposite end of the tube 12, where the cutting head 16 has an up curving configuration and orientation relative to the tube 12, as shown. The tube 12 has an offset curved section 20 that provides the surgeon with greater visibility of the cutting head 16 when he is holding the handle 14 during the surgical procedure. In one non-limiting embodiment, the tube 12 has a 10 or 12 French sized diameter suitable for the minimally invasive surgical procedure.

FIG. 3 is a broken-away perspective view of the end of the knife 10 including the cutting head 16. A blade 22 is rigidly mounted within a suitable slot in a top surface of the cutting head 16. The cutting head 16 is curved relative to the tube 12 with any degree of curvature suitable for the various anatomies that may be severed during the various surgical procedures. The knife 10 includes a suction inlet port 24 formed in the cutting head 16. The suction port 24 is provided at a tip of the cutting head 16 in this embodiment. However, in other embodiments, the port 24 may be provided at other locations in the cutting head 16. As will be discussed below, the cutting head 16 allows the surgeon to sever various anatomies and structures during the surgical procedure, and the suction capability of the knife 10 allows blood and other materials to be drawn from the surgical area through the tube 12 during the surgical procedure.

The cutting head 16 can be fixed or mounted to the tube 12 by any suitable technique, such as gluing or welding, so that the inlet port 24 is in fluid communication with the bore 18 through a suitable chamber in the head 16. Alternately, the cutting head 16 can be mounted to the end of the tube 12 by any suitable snap fit and/or quick release type engagement. This would allow the cutting head 16 to be replaced with other cutting heads that may have blades for various and possibly different operations, such as blades having different curvatures, different lengths, different orientations, etc., and different types of blades, such as serrated blades, thicker blades, etc. Further, it may be possible to replace the cutting head 16 with other instruments for other procedures that may be benefit from the suction aspect of the device, such as a retractor, see U.S. patent application Ser. No. 12/981019, titled Minimally Invasive Suction Retractor, filed Dec. 29, 2010, assigned to the assignee of this application and herein incorporated by reference. FIG. 4 is a broken-away perspective view of an end of the knife 10 where the cutting head 16 is detachable and is shown separated from the tube 12 to illustrate this embodiment.

The handle 14 includes an internal chamber 30 that is in fluid communication with the bore 18 extending through the tube 12. The handle 14 also includes a suction outlet port 32 in fluid communication with the chamber 30 at an end of the handle 14 opposite to the tube 12 that is attachable to a suction hose (not shown) and a suitable suction pumping system of the type well known to those skilled in the art. When the suction hose is coupled to the suction outlet port 32, suction is provided to the surgical area to draw material through the inlet port 24. In this embodiment, the handle 14 includes a thumb vent 34 in fluid communication with the chamber 30 that allows the surgeon to control the suction, where suction is provided when the surgeon places his thumb over the vent 34 and suction is removed when the surgeon removes his thumb from the vent 34. The handle 14 is shown to have a cylindrical shape in this embodiment. However, as will be appreciated by those skilled in the art, the handle 14 can have any ergonomical shape suitable for the procedures being discussed herein. The tube 12, the cutting head 16 and the handle 14 can be made of any material suitable for the purposes described herein, such as stainless steel, peek, etc.

The cutting head 16 at the end of the knife 10 is oriented so that it extends up so that the blade 22 faces the tube 12. This orientation of the cutting head 16 may be suitable for many of the surgical procedures. However, for other surgical procedures, it may be desirable to provide the cutting head 16 in an opposite orientation. To illustrate this embodiment, FIG. 5 shows a perspective view of an up-cutting knife 40 similar to the knife 10, where like elements are identified by the same reference numeral. In this embodiment, the cutting head 16 has been replaced with a cutting head 42 that extends in an opposite direction than the head 16. If the cutting head 16 is removable, as shown in FIG. 4, then it may be possible simply to remove the cutting head 16 from the tube 12, and reinsert the cutting head 16 into the tube 12 in a different orientation.

The foregoing discussion discloses and describes merely exemplary embodiments of the present invention. One skilled in the art will readily recognize from such discussion and from the accompanying drawings and claims that various changes, modifications and variations can be made therein without departing from the spirit and scope of the invention as defined in the following claims.

What is claimed is:

1. A surgical knife comprising:
   an elongated tubular portion having a bore extending therethrough;
   a handle portion having an internal chamber, said handle portion being coupled to an end of the tubular portion so that the chamber and the bore are in fluid communication with each other, said handle portion further including an outlet suction port in fluid communication with the chamber; and
   a curved blade head portion mounted to an end of the tubular portion opposite from the handle portion, said head portion including an inlet suction port in fluid communication with the bore and a blade mounted to a surface of the head portion, wherein the inlet suction port is in a tip of the blade head portion at a location that is more distal than the blade and, wherein material that enters the inlet suction port is able to flow through the bore, into the chamber of the handle portion and out of the outlet suction port and, wherein the blade extends an entire length of the blade head portion from a location where the blade head portion is mounted to the end of the elongated portion to a distal tip of the blade head portion.

2. The knife according to claim 1 wherein the blade is mounted to the head portion so that it faces the tubular portion.

3. The knife according to claim 1 wherein the blade head portion is removable from the tubular portion.

4. The knife according to claim 3 wherein the blade head portion is coupled to the tubular portion by a snap fit engagement.

5. The knife according to claim 1 wherein the tubular portion includes a curved section that causes the handle portion to be offset relative to the head portion.

6. The knife according to claim 1 wherein the handle portion includes a vent in fluid communication with the chamber.

7. The knife according to claim 1 wherein the outlet suction port is in an end of the handle portion opposite to the tubular portion.

8. The knife according to claim 1 wherein the handle portion is cylindrical.

9. A surgical knife comprising:
   an elongated portion;
   a handle portion being coupled to an end of the elongated portion;
   a curved blade head portion mounted to an end of the elongated portion opposite from the handle portion, said head portion including a blade mounted to a surface of the head portion facing the elongated portion and said head portion being curved so that it curves upward, wherein the blade extends an entire length of the blade head portion from a location where the blade head portion is mounted to the end of the elongated portion to a distal tip of the blade head portion; and an inlet suction port in a tip of the blade head portion at a location that is more distal than the blade.

10. The knife according to claim 9 wherein all of the elongated portion, the handle portion and the head portion include chambers that are in fluid communication with each other, said handle portion including an outlet port.

11. The knife according to claim 10 wherein the outlet port is in an end of the handle portion opposite to the elongated portion.

12. The knife according to claim 9 wherein the blade head portion is removable from the elongated portion.

13. The knife according to claim 12 wherein the blade head portion is coupled to the tubular portion by a snap fit engagement.

14. The knife according to claim 9 wherein the elongated portion includes a curved section that causes the handle portion to be offset relative to the head portion.

15. The knife according to claim 9 wherein the handle portion is cylindrical.

16. A surgical process comprising:
   providing a surgical knife including an elongated tubular portion having a bore extending therethrough, a handle portion having an internal chamber, said handle portion being coupled to an end of the tubular portion so that the chamber and the bore are in fluid communication with each other, said handle portion further including an outlet suction port in fluid communication with the chamber, and a curved blade head portion mounted to an end of the tubular portion opposite from the handle portion, said head portion including an inlet suction port in fluid communication with the bore and a blade mounted to a surface of the head portion, wherein the inlet suction port is in a tip of the blade head portion at a location that is more distal than the blade and, wherein the blade extends an entire length of the blade head portion from a location where the blade head portion is mounted to the end of the elongated portion to a distal tip of the blade head portion; and using the knife during the surgical process to simultaneously remove the material from a surgical area and cut a structure from the surgical area.

17. The process according to claim 16 wherein the blade is mounted to the head portion so that it faces the tubular portion.

18. The process according to claim 16 wherein the blade head portion is removable from the tubular portion.

* * * * *